US008349588B2

(12) United States Patent
De Boer et al.

(10) Patent No.: US 8,349,588 B2
(45) Date of Patent: *Jan. 8, 2013

(54) RECOMBINANT XRGD-ENRICHED GELATINS HAVING HIGH STABILITY

(75) Inventors: Arjo Lysander De Boer, Tilburg (NL); Hendrik Van Urk, Tilburg (NL); Jan Bastiaan Bouwstra, Tilburg (NL); Peter Franciscus Theresius Maria Van Asten, Tilburg (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 311 days.

This patent is subject to a terminal disclaimer.

(21) Appl. No.: 12/527,937

(22) PCT Filed: Feb. 21, 2008

(86) PCT No.: PCT/NL2008/050100
§ 371 (c)(1),
(2), (4) Date: Aug. 20, 2009

(87) PCT Pub. No.: WO2008/103042
PCT Pub. Date: Aug. 28, 2008

(65) Prior Publication Data
US 2010/0075902 A1 Mar. 25, 2010

(30) Foreign Application Priority Data

Feb. 21, 2007 (EP) .................................. 07102838
Feb. 21, 2007 (EP) .................................. 07102839
Sep. 12, 2007 (EP) .................................. 07116189
Sep. 12, 2007 (EP) .................................. 07116193
Jan. 16, 2008 (EP) .................................. 08100556

(51) Int. Cl.
*C12P 21/06* (2006.01)
*C07K 14/00* (2006.01)

(52) U.S. Cl. ............................. 435/69.1; 530/350; 514/1

(58) Field of Classification Search .................. 530/350; 514/1; 435/69.1
See application file for complete search history.

(56) References Cited

U.S. PATENT DOCUMENTS

| | | | |
|---|---|---|---|
| 4,855,134 A | 8/1989 | Yamahira et al. | 424/85.7 |
| 5,002,769 A | 3/1991 | Friedman | 424/422 |
| 5,023,082 A | 6/1991 | Friedman et al. | 424/426 |
| 5,399,361 A | 3/1995 | Song et al. | 424/486 |
| 5,512,301 A | 4/1996 | Song et al. | 424/484 |
| 5,597,578 A | 1/1997 | Brown et al. | 424/422 |
| 5,733,994 A | 3/1998 | Koepff et al. | 527/207 |
| 5,897,879 A | 4/1999 | Friedman et al. | 424/486 |
| 6,068,854 A | 5/2000 | Wunderlich et al. | 424/464 |
| 6,140,072 A | 10/2000 | Ferrari et al. | 435/69.1 |
| 6,150,081 A | 11/2000 | Van Heerde et al. | 430/569 |
| 6,342,250 B1 | 1/2002 | Masters | 424/484 |
| 6,458,386 B1 | 10/2002 | Schacht et al. | 424/488 |
| 6,831,058 B1 | 12/2004 | Ikada et al. | 514/2 |
| 6,992,172 B1 | 1/2006 | Chang et al. | 530/354 |
| 7,517,954 B2 | 4/2009 | Bouwstra et al. | 530/350 |
| 7,598,347 B2 * | 10/2009 | Bouwstra et al. | 530/350 |
| 2002/0028243 A1 | 3/2002 | Masters | 424/484 |
| 2002/0106410 A1 | 8/2002 | Masters | 424/484 |
| 2003/0007991 A1 | 1/2003 | Masters | 424/423 |
| 2003/0064074 A1 | 4/2003 | Chang et al. | 424/184.1 |
| 2004/0237663 A1 | 12/2004 | Farber et al. | 424/488 |
| 2005/0058703 A1 | 3/2005 | Chang et al. | 424/456 |
| 2005/0119170 A1 | 6/2005 | Bouwstra et al. | 514/12 |
| 2005/0147690 A1 | 7/2005 | Masters et al. | 424/499 |
| 2005/0208141 A1 | 9/2005 | Farber et al. | 424/488 |
| 2005/0229264 A1 | 10/2005 | Chang et al. | 800/8 |
| 2005/0238663 A1 | 10/2005 | Hunt | 424/239.1 |
| 2006/0024346 A1 | 2/2006 | Brody et al. | 424/423 |
| 2006/0024361 A1 | 2/2006 | Odidi et al. | 424/464 |
| 2006/0068013 A1 | 3/2006 | DiTizio et al. | 424/484 |
| 2006/0121609 A1 | 6/2006 | Yannas et al. | 435/395 |
| 2006/0147501 A1 | 7/2006 | Hillas et al. | 424/443 |
| 2006/0177492 A1 | 8/2006 | Yunoki et al. | 424/445 |
| 2006/0204511 A1 | 9/2006 | Bouwstra et al. | 424/185.1 |
| 2006/0241032 A1 | 10/2006 | Bouwstra et al. | 514/12 |
| 2006/0251719 A1 | 11/2006 | Tabata | 424/468 |
| 2007/0004034 A1 | 1/2007 | Bouwstra et al. | 435/289.1 |
| 2007/0009580 A1 | 1/2007 | DiCosmo et al. | 424/443 |
| 2007/0031501 A1 | 2/2007 | Van Es et al. | 424/488 |
| 2007/0190153 A1 | 8/2007 | Farber | 424/488 |
| 2007/0196496 A1 | 8/2007 | Farber et al. | 424/488 |

(Continued)

FOREIGN PATENT DOCUMENTS

JP 2005-211477 8/2005

(Continued)

OTHER PUBLICATIONS

Werten et al., "High-yield Secretion of Recombinant Gelatins by *Pichia pastoris*", Yeast, 15:1087-1096 (1999).
Báez et al., "Recombinant microbial systems for the production of human collagen and gelatin", Appl. Microbio! Biotechnol., 69:245-252 (2005).
Werten et al., "Secreted production of a custom-designed, highly hydrophilic gelatin in *Pichia pastoris*", Protein Engineering, 14(6):447-454 (2001).
Olsen et al, "Recombinant collagen and gelatin for drug delivery", Advanced Drug Delivery Reviews, Amsterdam, NL, 55(12):1547-1567 (2003).
Sutter et al., "Recombinant gelatin hydrogels for the sustained release of proteins", Journal of Controlled Release, 119:301-312 (2007).
Extracts from gmap-gelatin.com, dated Aug. 25, 2006.

(Continued)

*Primary Examiner* — Karen Cochrane Carlson
(74) *Attorney, Agent, or Firm* — Morgan, Lewis & Bockius LLP

(57) ABSTRACT

The invention concerns recombinant gelatin monomers and recombinant gelatins comprising or consisting of multimers of the monomers. The recombinant gelatins are of particular use in several applications involving cell attachment such as in cell culture work and applications involving cell cultures of anchor dependent cells and also in a variety of medical applications.

10 Claims, No Drawings

U.S. PATENT DOCUMENTS

| | | | |
|---|---|---|---|
| 2008/0107666 A1 | 5/2008 | van Es et al. | 424/185.1 |
| 2008/0113910 A1 | 5/2008 | Bouwstra et al. | 514/12 |
| 2008/0114078 A1 | 5/2008 | Bouwstra et al. | 514/774 |
| 2008/0167446 A1 | 7/2008 | Bouwstra et al. | 530/354 |
| 2008/0274957 A1 | 11/2008 | Bouwstra et al. | 514/12 |
| 2009/0143568 A1 | 6/2009 | Chang et al. | 530/354 |

FOREIGN PATENT DOCUMENTS

| | | |
|---|---|---|
| WO | WO 2004/056976 | 7/2004 |
| WO | WO 2004/085473 | 10/2004 |
| WO | WO 2005/011739 | 2/2005 |
| WO | WO 2007/073190 | 6/2007 |

* cited by examiner

RECOMBINANT XRGD-ENRICHED GELATINS HAVING HIGH STABILITY

This is a 371 filing based on PCT/NL08/050100 filed Feb. 21, 2008 and claiming priority from European Application No. 07102838.5, filed Feb. 21, 2007; European Application No 07102839.3, filed Feb. 21, 2007; European Application No. 07116189.7, filed Sep. 12, 2007; European Application No. 07116193.9, fled Sep. 12, 2007 and European Application No. 08100556.3, filed Jan. 16, 2008.

FIELD OF THE INVENTION

The invention is in the field of recombinantly produced XRGD-enriched gelatins and methods of producing these. The gelatins of the present invention are of particular use in several applications involving cell attachment such as in cell culture work and applications involving cell cultures of anchor dependent cells and also in a variety of medical applications. In particular, the recombinant gelatins are highly stable, i.e. have a high resistance against proteolytic and/or chemical degradation. The high stability leads to a high yield when produced in recombinant host cells and is also advantageous in the later use of the proteins, for example in medical compositions or devices.

BACKGROUND OF THE INVENTION

Cell culture systems of animal cells, in particular mammalian cells (including human cells), are important for the production of many important (genetically engineered) biological materials such as vaccines, enzymes, hormones and antibodies. The majority of animal cells are anchorage-dependent and require attachment to a surface or cell culture support for their survival and growth.

Cell attachment also plays an important role in medical applications such as wound treatment (including artificial skin materials, but also sticking plasters or band-aids comprising compounds or compositions that promote healing and cell attachments), bone and cartilage (re)growth and implantations and artificial blood vessel materials. Thus in medical applications often the demand is that a material, such as an implant or transplant material, comprises a biocompatible coating in terms of cell attachment.

Another area of interest in relation to cell attachment is the blocking of attachment receptors of cells. For instance by blocking the attachment receptors cancer metastasis may be influenced or inhibited, platelet aggregation may be influenced in antithrombotic compositions and tissues adhesion may be prevented, e.g. after surgery, or may be promoted, e.g. for dental products or other medical products.

In US 2006/0241032 RGD-enriched gelatin-like proteins with a minimum (increased) level of RGD motifs and with a certain distribution of said RGD motifs are disclosed that were found to be highly suitable for cell adhesion and cell binding in medical and biotechnological applications. The cell binding peptides described therein have good cell attachment properties.

However, susceptibility to degradation has been a limiting factor in the ability to produce large amounts of recombinant gelatins.

EP 926543 and Werten et al. 1999 (Yeast 15, 1087-1096) describe a production method of recombinant gelatins, wherein high yields of non-hydroxylated fragments of the helical domain (consisting of Gly-Xaa-Yaa triplet repeats) of mouse type I (encoding a 21 kDa and 28 kDa, calculated mw, COL1A1 peptide and a 53 kDa COL1A2) and rat type III (COL3A1) are produced in the methylotrophic yeast *Pichia pastoris*. Yields were between 3-4 g/liter clarified broth and up to 14.8 g/liter for a multicopy transformant of COL3A1. For COL3A1 degradation could be reduced by changing the fermentation pH from pH 5 to pH 3. In contrast, this did not reduce degradation of COL1A1, which appeared to contain an endopeptidase motif (Met-Gly-Pro-Arg). Upon site-directed mutagenesis of this motif to Arg-Gly-Pro-Met, degradation was reduced and it was speculated that a Kex2 protease or a Kex2-like protease recognized the motif [Leu-Ile-Val-Met]-Xaa-Yaa-Arg. However, yields of COL1A1 sequences still need to be improved. Werten et al. hypothesize that the yield of COL1A1 remains below that of COL3A1 due to the codon usage of COL1A1 being different from that of highly expressed *P. pastoris* genes, while the codon usage of COL3A1 is similar to that of highly expressed *P. pastoris* genes.

SUMMARY OF THE INVENTION

The instant invention has now found ways for improving yield and/or stability of XRGD-enriched gelatin-like sequences, such as sequences consisting of or comprising Gly-Xaa-Yaa triplets, for example sequences consisting of or comprising all or part of the triple helix domain (also referred to as the "collagenous domain") of collagen (such as mammalian, especially human, COL1A1), or sequences essentially similar thereto. It was found that the sequence DRGD (Asp-Arg-Gly-Asp) and PRGD (Pro-Arg-Gly-Asp) should not be present, i.e. that XRGD (Xaa-Arg-Gly-Asp) should be present in a minimal amount, whereby X (Xaa) is any amino acid, except for D (Asp), P (Pro) or hydroxyproline. The instant invention provides thereby greatly stabilized gelatine-like polypeptides, which can be produced at high levels and which are particularly useful for cell attachment.

In one embodiment of the invention an XRGD-enriched recombinant gelatin polypeptide is provided, the amino acid sequence of which is free of the motifs DRGD and/or PRGD but comprises at least one XRGD motif, where X is any amino acid with the exception of D (Asp) and P (Pro) or O (hydroxyproline). Such sequences have greatly enhanced stability to chemical and/or proteolytic degradation.

The stability and expression level of RGD enriched gelatine-like sequences (and variants thereof and fragments of any of these) can be significantly improved by expressing natural or synthetic nucleic acid sequences which have at least 60%, more preferably at least 70 or 80%, such as at least 90%, preferably at least 92%, 93%, 94%, 95%, 96%, 97%, 98% or 99% or more amino acid sequence identity to the collagenous domain of human COL(1)α1 (also written herein as COL1A1; see SEQ ID NO: 1) and/or to SEQ ID NO: 2 (CBE monomer) and which contain the sequence XRGD, preferably at least once, more preferably at least 2×, 3×, 4×, 5× or more, wherein X is any amino acid except D, P or O Provided are nucleic acid sequences (DNA or RNA), substantially pure recombinant gelatine-like polypeptide molecules and methods of producing such heterologous polypeptides at high yields and using large scale fermentation methods. Also compositions and devices consisting of or comprising such polypeptides are provided.

Also provided are multimers of such nucleic acid sequences and of the encoded polypeptides, so that the nucleic acid sequence encoding the XRGD-comprising monomer polypeptide unit is repeated several times, e.g. at least about 2-10 times, 20 times, 30 times, 50 times or 100 times, depending on the size of the monomer. Preferably the monomer or multimer has a calculated is molecular weight of at least about 15 kDa, 20 kDa, 30 kDa or more, such as 100 kDa, 50 kDa. Thus polypeptides (monomers or polymers) consisting of GXY triplets and having a molecular weight of about 15 kDa to about 150 kDa (and any value inbetween) are encompassed herein, wherein said polypeptides comprise at least one, but preferably more) XRGD motif, where X is any amino acid with the exception of D (Asp) and P (Pro) or O (hydroxyproline). Such monomeric and/or multimeric polypeptides are particularly suitable for cell adhesion applications.

Thus, in one embodiment of the invention, the recombinant XRGD-enriched gelatins are provided, as well as cell supports coated therewith and controlled release compositions comprising the recombinant gelatins. Also methods for using the recombinant gelatins and/or the cell supports or controlled release compositions for cell adhesion related medical applications are provided.

General Definitions

Whereas often the terms 'collagen', 'collagen-related', 'collagen-derived' or the like are also used in the art, the term 'gelatin' or 'gelatin-like' protein will be used throughout the rest of this description. Natural gelatin is a mixture of individual polymers with MW's ranging from 5,000 up to more than 400,000 daltons.

The terms "cell adhesion" and "cell attachment" are used interchangeably. Also the terms "XRGD sequence" and "XRGD motif" and "Xaa-Arg-Gly-Asp" are used interchangeably. The term "XRGD-enriched" refers herein to amino acid sequences comprising at least one XRGD motif, wherein X is not D, P or hydroxyproline (O). The term "XRGD-enriched" in the context of this invention means that the a certain level of XRGD motifs, calculated as a percentage of the total number of amino acids per molecule is present and that there is a certain even distribution of XRGD sequences in the amino acid sequence. The level of XRGD sequences is expressed as a percentage. This percentage is calculated by dividing the number of XRGD motifs divided by the total number of amino acids and multiplying the result with 100. The number of XRGD motifs is an integer starting from 1, 2, 3, . . . etc. In particular "XRGD-enriched" refers herein to amino acid sequences wherein the percentage of XRGD motifs related to the total number of amino acids is at least 0.4 and if the amino acid sequence comprises 350 amino acids or more, each stretch of 350 amino acids contains at least one XRGD motif. Preferably the percentage of XRGD motifs is at least 0.6, more preferably at least 0.8, more preferably at least 1.0, more preferably at least 1.2 and most preferably at least 1.5.

A percentage XRGD motifs of more than at least 0.4 corresponds with more than at least 1 XRGD sequence per 250 amino acids. The number of XRGD motifs is an integer, thus to meet the feature of 0.4%, an amino acid sequence consisting of 251 amino acids should comprise at least 2 XRGD sequences. Preferably the XRGD-enriched recombinant gelatins of the invention comprise at least 2 RGD sequence per 250 amino acids, more preferably at least 3 RGD sequences per 250 amino acids, most preferably at least 4 RGD sequences per 250 amino acids. In a further embodiment an XRGD-enriched gelatine according to the invention comprises at least 4 XRGD motifs, preferably 6, more preferably 8, even more preferably 12 up to and including 16 ROD motifs.

The expressions "triple helical domain" and "collagenous domain" are used interchangeably, and refer to the Gly-Xaa-Yaa triplet repeat region of the recombinant or natural collagen, i.e. [Gly-Xaa-Yaa]n, wherein Xaa and Yaa are any amino acid and wherein n is at least 5, 10, 15, 20, 30, 40, 50, 70, 80, 90, 100 or more. For example in natural human COL1A1 as depicted in SEQ ID NO: 1, the collagenous domain is from amino acid 179 to amino acid 1192, the whole of which or a variant or a fragment of which (or of the variant) may be used herein.

A "fragment" is a part of a longer nucleic acid or polypeptide molecule, which comprises or consist of e.g. at least 10, 15, 20, 25, 30, 50, 100, 200, 500 or more consecutive nucleotides or amino acid residues of the longer molecule.

"Native" or "natural" collagens or collagenous domains refer to those nucleic acid or amino acid sequences found in nature, e.g. in humans or other mammals.

"Variants" refer to sequences which differ from natural sequences by one or more amino acid insertions, deletions or replacements, and are "substantially identical" to the native sequences as defined below.

The terms "protein" or "polypeptide" or "peptide" are used interchangeably and refer to molecules consisting of a chain of amino acids, without reference to a specific mode of action, size, 3-dimensional structure or origin. An isolated protein is a protein not found in its natural environment, such as a protein purified from a culture medium.

The term "support" or "cell attachment support" refers herein to any support which can be used to facilitate cell attachment and/or growth, such as culture dishes, microcarriers (e.g. microcarrier beads), stents, implants, plasters, etc.

The term "substantially identical", "substantial identity" or "essentially similar" or "essential similarity" means that two polypeptide, when aligned pairwise using the Smith-Waterman algorithm with default parameters, comprise at least 60%, 70%, 80%, more preferably at least 90%, 95%, 96% or 97%, more preferably at least 98%, 99% or more amino acid sequence identity. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or using in EmbossWIN (e.g. version 2.10.0). For comparing sequence identity between two sequences, it is preferred that local alignment algorithms are used, such as the Smith Waterman algorithm (Smith T F, Waterman M S (1981) J. Mol. Biol 147(1); 195-7), used e.g. in the EmbossWIN program "water". Default parameters are gap opening penalty 10.0 and gap extension penalty 0.5, using the Blosum62 substitution matrix for proteins (Henikoff & Henikoff, 1992, PNAS 89, 915-919).

The term "comprising" is to be interpreted as specifying the presence of the stated parts, steps or components, but does not exclude the presence of one or more additional parts, steps or components.

In addition, reference to an element by the indefinite article "a" or "an" does not exclude the possibility that more than one of the element is present, unless the context clearly requires that there be one and only one of the elements. The indefinite article "a" or "an" thus usually means "at least one".

"Monomer" refers to a polypeptide unit (or nucleic acid sequence encoding it) which can be used to generate a "multimer" (or "polymer", which is used interchangeably) by repeating the unit in a linear fashion to generate a longer polypeptide. The monomer units are preferably repeated without intervening amino acids, although optionally 1, 2, 3, 4, 5 or more linking amino acids may be present between monomer units.

The term "improved stability" means that an XRGD-enriched gelatine is not hydrolysed or is hydrolysed to a lesser extent, preferably by at least a factor 2, under usual culture conditions of the yeast expression host compared to the corresponding sequence having DRGD, PRGD or ORGD (O meaning hydroxyproline).

DETAILED DESCRIPTION OF THE INVENTION

It was found, surprisingly, that it is possible to obtain high yields of improved, highly stable peptides or polypeptides with excellent cell attachment properties and which comprise advantages such as improved stability, improved cell attachment properties (probably due to the improved stability) and/or result in a more homogenous distribution of particle size of carriers coated with the recombinant polypeptides (such as core microcarrier beads).

The polypeptides also do not display any health related risks, as they have a low antigenicity and that can be used without the risk of transferring pathological factors such as viruses, prions and the like.

Especially stability and yield of full length, non-degraded XRGD enriched protein in methylotrophic yeasts (especially of the genus *Pichia* or *Hansenula*) could be improved by expressing a nucleic acid sequence encoding an XRGD-enriched gelatine like polypeptide. The recombinant XRGD-enriched polypeptide comprises or consists of a suitable number of consecutive GXY triplets, so that the size of the polypeptide (monomer or polymer) is between about 15 kDa and about 150 kDa. In one embodiment the recombinant gelatine-like polypeptide (i.e. the monomer and/or the multimer) has at least 60% sequence identity to the collagenous domain of human COL1A1 (amino acids 179 to 1192 of SEQ ID NO:1) and/or to SEQ ID NO: 2 and that does not contain the sequences DRGD and/or PROD but does contain a minimal number of XRGD motifs (at least one), where X can be any amino acid except D and P or O (hydroxyproline).

Gelatin-like Polypeptide Monomers According to the Invention

Thus, in one embodiment of the invention a recombinant ROD-enriched gelatin monomer is provided, which is free of the motifs DRGD or PROD or ORGD but comprising at least one XRGD motif, where X is any amino acid with the exception of D (Asp) and P (Pro) or O (hydroxyproline).

Alternatively or in addition, the recombinant XRGD-enriched gelatine like protein can also be defined by sequence identity to SEQ ID NO: 1 and/or SEQ ID NO: 2, as a protein comprising or consisting of an amino acid sequence having at least 60%, preferably at least 70%, 80%, 90% or more amino acid sequence identity to amino acids 179-1192 of SEQ ID NO: 1 or to a fragment thereof such as a fragment of at least 15 consecutive amino acids, more preferably at least 92%, 95%, 96%, 98%, 99% sequence identity or more. "Fragments" are parts of less than 1000 amino acids, such as 800, 600, 500, 300, 250, 200, 100, 50, 30 or less consecutive amino acids, but preferably at least 10, 15 or 20 amino acids.

Preferably said sequence comprises at least 1 XRGD motif, more preferably at least 2 XRGD motifs, whereby X may be any amino acid but is not D, P or O (hydroxyproline). The polypeptide is preferably free of any DRGD, PRGD and ORGD sequence motif. Thus, for example nucleic acid sequences encoding natural COL1A1 collagenous domains may be used (e.g. from mammalian type I procollagens, such as mouse, rat, human COL1A1 genes) and the codons encoding the natural. DRGD motif and/or PROD motif may be modified, e.g. by site directed mutagenesis, into XRGD. Alternatively, the DRGD and/or PRGD motifs may be modified into a different sequence so that the polypeptide is free of these motifs and at least one or more 'new' XRGD motifs may be introduced anywhere in the sequence. Of course it is also possible to simply design amino acid sequences comprising consecutive GXY motifs, such as at least 5, 10, 15, 20, 30, 50, 100, 200, 300 or more consecutive GXY motifs, whereby at least one, but preferably more XRGD motifs are included in the sequence. Such designed polypeptides can be made by making nucleic acid sequences encoding these (using routine molecular biology techniques) and expressing these in a recombinant host cell. Preferably the spacing of the XRGD motifs (with X not being D or P or O) is such that at least about 0, 10, 15, 20, 25, 30 or more intervening amino acids are present (see below). When several XRGD-motifs are present in the sequence, these are preferably spaced regularly, although this is not a requirement.

Although X may be any amino acid, except D, P and O, X is preferably selected from C, M, K, L, I, R, K, H, S, T, V, A, G or E. Preferably X sleeted from S, T, V, A, G and E. Most preferably X is E. When more than one XRGD present, the X present in the different XRGD motifs need not be the same, although in a preferred embodiment all XRGD motifs are ERGD. Thus, a preferred recombinant gelatine comprises or consists of an amino acid sequence having at least 60% sequence identity to amino acids 179-1192 of SEQ ID NO: 1 and/or to a fragment thereof and/or to SEQ ID NO: 2, is preferably free of DRGD and/or PRGD (and ORGD), comprises at least one, preferably at least 2, preferably at least 3 or more XRGD motifs, wherein X is preferably E in at least one, but preferably in at least two or in all XRGD motifs present in the sequence. In one embodiment a large number of XRGD motifs is present, such as at least 10, 20, 30, or more. Optionally the entire monomer is composed of XRGD motifs linked consecutively, with 0, 1, 2, 3, 4, or 5 intervening amino acids between motifs.

Preferably, the XRGD motifs are part of the GXY motifs, i.e. the GXY triplets are not disrupted by the XRGD motif(s). For example in a sequence—GXY-GXY-GXR-GDY-GXY-GXY—the XRGD motif does not disrupt the consecutive GXY triplets.

Thus, also more than 2 XRGD motifs may be present in the monomer polypeptide, such as 3, 4, 5 or more, wherein X is again any amino acid except D, P or O. Such further XRGD motifs can also be introduced into natural sequences, e.g. by site directed mutagenesis or using other methods.

It is a further embodiment that the recombinant gelatine does not contain any S (Ser) and/or T (Thr) and/or N (Asn). Thus, for example S and/or T and/or N found in natural collagen domains (or fragments thereof) may be replaced and/or deleted using known molecular biology methods. Alternatively, natural fragments may be selected which are free of S and/or T and/or N. Glycosylation is thereby reduced or prevented (see further below).

Preferably, the XRGD motifs are distributed relatively evenly within the sequence, especially if additional XRGD motifs are introduced. The spacing between the natural DRGD (amino acids 744-777 of SEQ ID NO: 1) and PRGD (amino acids 1092-1095 of SEQ ID NO: 1), which are in a preferred embodiment modified into XRGD, with X not being D or P or O, is 344 intervening amino acids. Additional XRGD motifs may be introduced so that a spacing of at least about 30, 45, 50 100 intervening amino acids or more is found between XRGD motifs. Thus, the polypeptide comprises preferably at least 2 or more XRGD motifs per 100, 150, 200 or 300 or 350 amino acids. Optionally more XRGD and/or ERGD motifs may be present, such as 5, 6, 7, 8, 9, 10 or more.

In one embodiment the recombinant gelatine like protein is a polymer (used herein interchangeably with the term "multimer") which comprises or consists two or more of the monomers described above. Thus, the recombinant polymer may comprise n monomer units, each monomer fulfilling the above criteria, wherein n is the number of monomer repeats that is required to build a multimer of about 15 to 150 kDa. The value of n therefore depends on the size of the monomer. For a monomer of 10 amino acids, n may for example be 10 to 100, or more. For a monomer with 100 amino acids n may e.g. be 1 to 10. The polymer may comprise identical or different monomer units, linked consecutively. Each monomer preferably comprises at least one XRGD, wherein X is not D or P or O. As the monomers are free of DRGD and/or PRGD, the polymer is also free of these motifs. Preferably the polymer comprises at least n XRGD motifs (wherein X is not D, P or O) and no DRGD, PRGD or ORGD motifs. Preferably the polymer is also free of S, T and/or N.

The monomer units present in a polymer are in one embodiment identical in their amino acid sequence.

Although it is preferred that no intervening amino acids are present between the monomer units, also polymers comprising one or more intervening amino acids between monomer units are provided herein.

The stability to enzymatic and/or chemical proteolysis of the above polypeptides is higher than that of the corresponding natural polypeptides, e.g. the natural amino acids 179-1192 of SEQ ID NO: 1, or natural variants thereof or fragments thereof and/or higher than that of the corresponding amino acid sequence wherein the X of the XRGD motifs is D, P or O. For example, the stability of the XRGD-enriched CBE monomer of the Examples (SEQ. ID NO: 2) is higher than that of the corresponding CBT monomer (SEQ ID NO: 5) which has the same amino acid sequence as CBE but wherein X in the XRGD motif is D. The CBE monomer is not cleaved into smaller fragments during/after production in *Pichia*, but remains stable as one polypeptide, as seen by LC-MS.

Preferably no or reduced degadation or cleavage products, i.e. polypeptides of a smaller size than that of the encoded (full length) polypeptide, are seen in/after a stability assay, e.g. on SDS-PAGE gels or by other methods such as LC-MS. Stability can for example be tested after the polypeptide is secreted into the culture medium of the yeast host, whereby the polypeptide is stable if substantially all (at least 95%, preferably at least 98%, 99% or most preferably 100%) of the recombinant polypeptide is full size. In any case, the proportion of polypeptide which is not degraded is significantly higher than when producing the corresponding polypeptide, having D, P or O in the X position of the XRGD motif but having the same amino acid sequence otherwise, is treated in the same way, e.g. expressed in a recombinant host in the same way or is subjected to the same stability assays. Stability to enzymatic or chemical hydrolysis can be also be tested by incubating the polypeptide with one or more proteolytic enzymes or hydrolytic chemicals and by analysing the resulting molecular weight after a specified period of treatment.

For example, when the molecular weight of recombinant natural gelatins and gelatins according to the invention produced in the same yeast host is compared after fermentation, the recombinant gelatine according to the invention is less degraded than the natural gelatine produced under the same conditions and in the same way. Degradation can also be quantified, e.g. by analysing band intensities on SDS-PAGE gels loaded with the same amount of sample. See e.g. Werten et al. 1999 (supra).

The gelatine like protein monomer (and the polymer comprising or consisting of monomers) preferably comprises a substantial number, or consists of GXY triads, wherein G is Glycine and X and Y are any amino acid. A substantial number of GXY triads refers to at least about 50%, more preferably at least 60%, 70%, 80%, 90% or most preferably 100% of amino acid triplets of the whole polypeptide being GXY, especially consecutive GXY triplets. The N- and/or C-terminal end of the monomer and/or polymer may comprise other amino acids, which need not be GXY triplets. Also, the molecular weight of the monomer is preferably at least about 15 kDa (calculated molecular weight), more preferably at least about 16, 17, 18, 19, 20, 30, 40, 50, 60, 70, 80, 90 kDa or more.

In a preferred embodiment the XRGD-comprising gelatine is prepared by recombinant DNA technology, especially by expression of nucleic acid sequences in methylotrophic yeast, preferably *Pichia* and/or *Hansenula*, most preferably *Pichia pastoris*. The host is preferably not capable of hydroxylating proline, i.e. it lacks a functional prolyl-4-hydroxylase, so that in the resulting polypeptide less than 10%, more preferably less than 5%, less than 4%, less than 3 or 2%, most preferably less than 1% of the proline residues of the GXY triplets and/or of the total proline residues in the polymer are hydroxylated. Recombinant gelatines of this invention are preferably derived from natural collageneous sequences, preferably with further modification to fulfil the amino acid sequence criteria described elsewhere herein. Especially natural mammalian COL1A1 sequences are suitable for modification, such as mammalian procollagen COL1A1 sequences. These contain a single contiguous stretch of GXY triplets, which makes up the collagenous domain. Nucleic acid sequences encoding collagens, such as COL1A1, have been generally described in the art. (See, e.g., Fuller and Boedtker (1981) Biochemistry 20: 996-1006; Sandell et al. (1984) J Biol Chem 259: 7826-34; Kohno et al. (1984) J Biol Chem 259: 13668-13673; French et al. (1985) Gene 39: 311-312; Metsaranta et al. (1991) J Biol Chem 266: 16862-16869; Metsaranta et al. (1991) Biochim Biophys Acta 1089: 241-243; Wood et al. (1987) Gene 61: 225-230; Glumoff et al. (1994) Biochim Biophys Acta 1217: 41-48; Shirai et al. (1998) Matrix Biology 17: 85-88; Tromp et al. (1988) Biochem J 253: 919-912; Kuivaniemi et al. (1988) Biochem J 252: 633640; and Ala-Kokko et al. (1989) Biochem J 260: 509-516.) and are available from gene/protein databases.

Gelatin Like Polypeptide Multimers According to the Invention

In a further embodiment multimers of the above monomers are provided. Such multimers thus comprise or consist of at least 2, 3, 4, 5, 6, 7, 8, 9 or 10 repeats of the monomer sequence. This, in a further embodiment a recombinant gelatin polypeptide is provided comprising or consisting of a multimer of a monomer sequence described above. Preferably, the monomer repeats are repeats of the same monomer unit (having identical amino acid sequences), although optionally also combinations of different monomer units (having different amino acid sequences, each falling under the criteria above) may be used.

Preferably the monomer units are not separated by spacing amino acids, although short linking amino acids, such as 1, 2, 3, 4 or 5 amino acids, may also be inserted between one or more of the monomers.

In one embodiment the multimers comprise or consist of at least 2, 3, 4, 5, 6, 7, 8, 9 or 10 repeats of a monomer as described above, e.g. of a sequence substantially identical to amino acids 179-1192 of SEQ ID NO: 1, or a fragment thereof, wherein the sequence is free of DRGD and/or PRGD and wherein the sequence comprises at least one XRGD, with X not being D or P or O (see above).

Such multimers can be generated using known standard molecular biology methods.

Material and Compositions Comprising the XRGD-Comprising Monomers and/or Multimers The present invention is directed to peptides, polypeptides or proteins, in particular to recombinant gelatines or gelatine-like proteins, which are highly suitable for cell adhesion and can be used in medical or biotechnological applications. More specifically the invention is directed to cell binding peptides or polypeptides that have improved properties compared to known recombinant gelatine-like RGD-comprising poplypeptides, such as described in US2006/0241032, in particular the sequence designated as SEQ ID NO: 2 therein.

It was found that recombinant gelatines according to the invention are very suitable for coating cell culture supports which can be used in biotechnological processes or in medical applications.

XRGD sequences in gelatines can adhere to specific receptors on the cell wall called integrins. These integrins differ in their specificity in recognising cell binding amino acid sequences. Although both natural gelatine and, for example, fibronectin may contain XRGD sequences, gelatine can bind cells that will not bind to fibronectin and vice versa. Therefore fibronectin comprising XRGD sequences cannot always replace gelatine for cell adhesion purposes.

Recombinantly produced gelatine does not suffer from the disadvantage of animal-derived gelatine, i.e. potential contamination with pathogens originating from the animal from which the gelatine was derived.

When used as or in combination with a cell culture support, the gelatine-like polypeptides according to the invention functions as a cell binding polypeptide. It has the advantage over other polypeptides that it can also be metabolised by the cells growing on it.

A further advantage of recombinantly produced gelatines is that the molecular weight (MW) can be kept uniform. Natural gelatines unavoidably have a broad molecular weight distribution with peptides smaller than 5,000 kD up to large polymers with a molecular weight larger than 400,000 kD, resulting from the production method. In particular in combination with microcarrier core beads as cell culture support, a disadvantage of smaller peptides is that they will adhere inside finer pores of the microcarrier which cannot be reached by the cells so that part of the added gelatine is not used. With recombinant production methods the gelatine can be designed with the desired molecular weight, preventing this undesired loss of material.

A cell support comprising a recombinant gelatine according to the invention is provided. Such a cell support may be selected from the group consisting of
1) a cell-culture support, such as a core bead (e.g. a microcarrier bead) or a Petri dish or the like, coated with one or more gelatine-like polypeptides according to the invention;
2) an implant or transplant device (such as hip-, dental-, or other implants, stents, etc.) coated with one or more of the recombinant gelatins according to the invention,
3) a scaffold or matrix for tissue engineering, such as artificial skin matrix material, coated with one or more recombinant gelatine like polypeptides;
4) a wound healing product coated with one or more recommitment gelatine like polypeptides;
5) a tissue adhesive comprising or consisting of one or more recombinant gelatine like polypeptides;

The recombinant gelatine like proteins offers advantages in that the cell supports, such as microcarriers coated with the polypeptides, have advantageous properties. A key problem in the process of coating microcarrier core beads is the clumping together of beads. In particular such clumping reduces the available surface area for cell attachment and disturbs the size distribution of the microcarriers rendering them unusable. It was found that the use of the polypeptides according to the invention resulted in a more homogenous distribution of coated particle sizes. Also cell adhesion properties of the supports was improved, possibly due to the enhanced protein stability found.

In one embodiment the cell supports provided herein are preferably comprise only one recombinant gelatine according to the invention, i.e. selected from one of the polypeptides provided. The product is thus uniform in amino acid sequence, molecular weight, etc. Optionally the peptides may be cross-linked by e.g. chemical cross-linking.

In a different embodiment mixtures of polypeptides according to the invention may be used, such as 2, 3, 4, 5, or more different amino acid sequences according to the invention. The ratios of mixtures may vary, such as 1:1, or 10:1, 50:1, 100:1, 1:100, 1:50, 1:10, and ratios in between these. Optionally also these mixtures or parts thereof may be crosslinked by e.g. chemical cross linking.

In one embodiment solely recombinant gelatine polypeptides according to the invention are used in the cell support systems, i.e. other recombinant gelatins, such as those described in the prior art, or natural gelatins are not comprised in the cell support. In a different embodiment the cell support system may comprise further recombinant and/or natural gelatins (e.g. extracted from natural sources).

When sing the recombinant gelatine monomer(s) and/or multimers for coating porous microcarrier beads, preferably polypeptides with a molecular weight of at least about 30 kDa are used, e.g. at least about 30 kDa, 40 kDa, 50 kDa, 70 kDa or more. The reason for this is that smaller polypeptides enter the pores, thereby not contributing to the cell attachment properties of the coated beads and the coating process may be inefficient, especially if low concentrations of polypeptides are used in the process.

Preferably the molecular weight of the gelatine or gelatine-like protein used is uniform, with more than 75%, preferably more than 85%, more preferably more than 95% or even at least 98% of the gelatine or gelatine-like protein having a uniform MW within 20% from the selected molecular weight.

By selecting a molecular weight, within the above specified range, in a coating process the viscosity of the gelatine or gelatine-like protein coating solution can be accurately controlled. Complete or, more important, partial gelling of such a gelatine solution can be prevented while being able to select a high as possible concentration of the gelatine. The uniform gelatine ensures a process of identically coated microcarriers. The uniform coating process allows the use of a minimum amount of gelatine and the use of a minimum volume of gelatine coating solution. All this results in a far more efficient coating process than that is known in the art.

In one embodiment of the invention non-porous core beads are coated with gelatine of the invention. Suitably non-porous core beads are made of polystyrene or glass. Other suitable non-porous materials are known to those skilled in the art.

A particular advantageous embodiment is the process of the invention wherein porous core beads, such as beads from modified dextran or cross-linked cellulose, or (porous) polystyrene, in particular DEAE-dextran, are coated with gelatine of the invention. Other suitable porous materials are known to those skilled in the art, and include e.g. other chemically modified or non-modified polysaccharides.

The size of the beads may vary from 50 μm to 500 μm. Typical mean microcarrier bead sizes are about 100, about 150 or about 200 μm in physiological saline. Size ranges with at least 90% of the beads lying within the range may vary from 80-120 μm, 100-150 μm, 125-175 μm or 150-200 μm.

A wide range of cells may be cultured on microcarriers. For instance, cells from invertebrates, from fish, birds and cells of mammalian origin may be cultivated on microcarriers. Transformed and normal cell lines, fibroblastic and epithelial cells and even genetically engineered cells may be cultivated on microcarriers for various biological applications such as for the production of immunologicals like interferons, interleukins, growth factors etc. Cells cultured on microcarriers also serve as hosts for a variety of viruses that are used as vaccines like foot and mouth disease or rabies.

Microcarrier cultures have a wide number of applications other than mass cultivation as well. Cells growing on microcarriers serve as an excellent tool for studying different aspects of cell biology such as cell-to-cell or cell-to-substratum interactions. Cell differentiation and maturation, metabolic studies may also be carried out using microcarriers. Such cells can also be used for electron microscopic studies or for the isolation of cell organelles such as the cell membrane. Also, this system is essentially a three-dimensional system and serves as a good 3-D model. Similarly, co-cultivation of cells can be done using this system. Thus applications include the production of large quantities of cells, viruses and cell products (e.g. interferon, enzymes, nucleic acids, hormones), studies on cell adhesion, differentiation and cell function, perfusion column culture systems, microscopy studies, harvesting mitotic cells, isolation of cells, membrane studies, storage and transport of cells, assays involving cell transfer and studies on uptake of labelled compounds.

Microcarriers may also be used for the depletion of macrophages from a population of spleen cells. DEAE-dextran microcarriers can potentiate stimulation of lymphocytes by concanavalin A (con A). Microcarrier beads confluent with allogenic tumour cells can be injected in mice to increase humoral and cell-mediated immunity. Plant protoplasts can be immobilised on DEAE-dextran microcarriers.

As a result of the large surface area to volume ratio provided by microcarriers, they can successfully be used for a variety of biological productions on a laboratory scale as well as an industrial scale of for instance even 4000 liters or more.

Large scale production of expressed products can be accomplished with gelatine-coated microcarriers. Loading of microcarriers in production scale bioreaetors is generally 20 g/l, but may be increased up to 40 g/l. Microcarriers may be used in batch and perfusion systems, in stirred cultures, and wave bioreactors, as well as to increase the surface area of traditional stationary monolayers and roller cultures.

In a further preferred embodiment the gelatine or gelatine-like protein is in essence free of hydroxyproline residues. Hydroxylation is a requirement for the formation of triple helices in collagen and plays a role in gelation of gelatine. In particular less than 10%, more preferably less than 5% of the amino acid residues of the recombinant gelatines are hydroxyprolines, more preferably less than 1%, and most preferably the recombinant gelatine is free from hydroxyprolines in applications where the gelling capability of the recombinant gelatine is unfavourable. The hydroxyproline-free recombinant gelatines can be used in higher concentrations, and the solutions will be less viscous requiring less vigorous agitation, resulting in less shear forces on the cultured cells. As described in WO 02/070000 A1, recombinant gelatines which are is essence free from hydroxyprolines do not show immune reactions involving IgE in contrast to natural gelatine. Absence of hydroxyprolines can for example be achieved by expression in *Pichia* hosts, such as *Pichia pastoris*, which has not been transformed with or does not comprise a functional prolyl-4-hydroxlase enzyme.

A process for the preparation of collagen coated microcarriers is described in U.S. Pat. No. 4,994,388. In short providing a core bead with a collagen coating is performed in two steps: coating and fixing. The core beads are suspended in an acidic, aqueous collagen solution (0.01-0.1N acetic acid), and the solution is evaporated to dryness. The dry, collagen-coated beads are then suspended in a solution which contains a protein cross-linking agent such as glutaraldehyde, thus cross-linking the collagen coating. Alternatively, the core beads wetted with the collagen solution are not dried entirely before the start of the fixing step. Variations in coating conditions and alternative coating processes are well within the competence of those skilled in the art.

Recombinant structures can also be designed to incorporate additional positively charged groups, as in U.S. Pat. No. 5,512,474, by budding in additional arginines, lysines or histidines. Recombinant production of gelatines allows easy manipulation of the number of positively charged amino acids, meaning positively charged at the pH of the cell culture, in the produced protein. In particular arginine, lysine and histidine carry positive charges. It is well within the reach of the skilled person to design a gelatine with a net positive charge at the pH of the particular cell culture of interest. Cells are normally cultured at a pH of 7-7.5. Thus in a further embodiment of the invention a gelatine or gelatine-like protein is used that has a net positive charge at pH 7-7.5. Preferably the net positive charge is +2, +3, +4, +5, +10 or higher. Thus in a further embodiment the invention relates to a gelatine that has a net positive charge at pH 7-7.5. Preferably the net positive charge is +2, +3, +4, +5, +10 or higher In a further embodiment the invention relates to the use of XRGD-comprising gelatines according to the invention to block surface receptors on cells and to make compositions for blocking such receptors. Blocking of receptors of cells is applied in for example inhibiting angiogenesis or in blocking integrins on cardiac fibroblasts.

Cell supports coated with recombinant gelatine according to the invention, on which cells have been grown can be applied during, for example, transplantation of skin or wound treatment or to enhance hone or cartilage (re)growth. It is also possible to coat implant materials with recombinant gelatine of the invention to adhere cells which promote implantation.

In yet another embodiment of the invention a controlled release composition comprising one or more recombinant gelatins according to the invention is provided. The composition may, thus further comprise one or more drugs. Controlled release formulations can be made as known in the art, for example by using the recombinant gelatine-like proteins or compositions comprising these as a coating layer surrounding one or more drugs or for making a matrix in which the drug is enclosed or incorporated. The controlled release composition can be administered by injection (subcutaneous, intravenous or intramuscular) or orally or via inhalation. However, the used controlled release composition can also be implanted via surgery. Yet another suitable route of administering is via an external wound dressing or even transdermally.

The controlled release composition preferably comprises the recombinant gelatine in a cross-linked form, e.g. chemically crosslinked. The invention further provides use of a controlled release composition as described herein for the preparation of a medicament for the treatment of pain, cancer therapy, cardiovascular diseases, myocardial repair, angiogenesis, bone repair and regeneration, wound treatment, neural stimulation/therapy or diabetics.

In a further embodiment the invention relates to XRGD-comprising gelatines which are not glycosylated. Glycosylation takes place at the amino acids Asn (N-glycosydic structures), or Ser or Thr (O-glycosydic structures). Glycosylation should be preferably prevented for applications where no immune response is desired. The absence of Asn, Ser and/or Thr amino acids in the amino acid sequence is an effective way to prevent the glycosylation in biotechnological production systems using for instance yeast cell cultures.

Furthermore, characteristic for gelatine is the unusual high content of proline residues. Even more characteristic is that in natural gelatine a number of the proline residues is hydroxylated. Most prominent site of hydroxylation is the 4-position resulting in the presence in the gelatine molecule of the unusual amino acid 4-hydroxyproline. In mammals a triplet 4-hydroxyproline is always found in the Y position. The presence of the hydroxyproline residues is responsible for the fact that a gelatine molecule in its secondary structure can adopt a helical conformation. Thus, it is preferred that the gelatines to be used according to the invention in applications in which the gelling property is unfavourable contain less than 5%, preferably less than 3%, most preferably less than 1% of hydroxyproline residues.

The XRGD-comprising gelatines according to the invention can be produced by recombinant methods as disclosed in EP-A-0926543, EP-A-1014176 or WO01/34646. Also for enablement of the production and purification of gelatines of the invention reference is made to the examples in EP-A-0926543 and EP-A-1014176.

Starting from a natural nucleic acid sequence encoding (part of) a collagen, also point mutations can be applied so as to yield a sequence encoding XRGD comprising gelatine according to the invention and being free of DRGD and/or PRGD. Based on the known codons a point mutation can be performed so that an XRGX sequence after mutation will yield an XRGD sequence, alternatively also an XYGD sequence can be mutated to yield an XRGD sequence. Also it is possible to carry out two mutations so that an XYGX sequence will give an XRGD sequence. Also it may be possible to insert one or more nucleotides or delete one or more nucleotides giving rise to a desired XRGD sequence. In the same way DRGD and/or PRGD motifs can be removed, by e.g. replacing, inserting or deleting one or more of the amino acids. In addition it is possible to obtain a gene encoding the desired gelatine by gene synthesis. Gene synthesis services are offered by various companies.

Thus the gelatine-like proteins can be produced by expression of nucleic acid sequence encoding such polypeptide by a suitable micro-organism. The process can suitably be carried out with a fungal cell or a yeast cell. Suitably the host cell is a high expression host cells like *Hansenula, Trichoderma, Aspergillus, Penicillium, Saccharomyces, Kluyveromyces, Neurospora* or *Pichia*. Fungal and yeast cells are preferred to bacteria as they are less susceptible to improper expression of repetitive sequences. Most preferably the host will not have a high level of proteases that attack the collagen structure expressed. In this respect *Pichia* or *Hansenula* offers an example of a very suitable expression system. Use of *Pichia pastoris* as an expression system is disclosed in EP-A-0926543 and EP-A-1014176. In one embodiment the micro-organism is free of active post-translational processing mechanism such as in particular hydroxylation of proline and also hydroxylation of lysine. In another embodiment the host system has an endogenic proline hydroxylation activity by which the recombinant gelatine is hydroxylated in a highly effective way. The selection of a suitable host cell from known industrial enzyme producing fungal host cells specifically yeast cells on the basis of the required parameters described herein rendering the host cell suitable for expression of recombinant gelatine-like proteins suitable in compositions according to the invention in combination with knowledge regarding the host cells and the sequence to be expressed will be possible by a person skilled in the art.

Thus, in one aspect the invention concerns a method for producing a recombinant gelatine according to present invention, said method comprising
 preparing an expression vector comprising a nucleic acid sequence encoding a polypeptide according to claims 1-10 operably linked to a suitable promoter,
 expressing said nucleic acid sequence in a methylotrophic yeast,
 culturing said yeast under suitable fermentation conditions to allow expression of said nucleic acid sequence;
 optionally purifying said polypeptide from the culture.

Also mutant host strains may be used, e.g. strains deficient in one or more proteolytic enzymes, although this is not necessary according to the present invention, as the recombinant polypeptides are highly stable and resistant to proteolysis.

Sequences
SEQ ID NO 1: human procollagen COL1A1 sequence
SEQ ID NO 2: ERGD-enriched monomer
SEQ ID NO 3: ERGD-enriched multimer (trimer)
SEQ ID NO 4: ERGD-enriched multimer (pentamer)
SEQ ID NO 5: DRGD-comprising sequence
SEQ ID NO 6: ERGD-comprising sequence

EXAMPLES

Example 1

An XRGD-comprising gelatine was produced based on a nucleic acid sequence that encodes for a part of the gelatine amino acid sequence of human COL1A1-1 and modifying this nucleic acid sequence. The methods as disclosed in EP-A-0926543, EP-A-1014176 and WO01/34646 were used. This XRGD-comprising gelatine has the following sequence.

```
Amino acid sequence (SEQ ID NO: 6):
GAPGAPGLQGAPGLQGMPGERGAAGLPGPKGERGDAGPKGADGAPGAPGL

QGMPGERGAAGLPGPKGERGDAGPKGADGAPGKDGVRGLAGPIGPPGERG

AAGLPGPKGERGDAGPKGADGAPGKDGVRGLAGPIGPPGPAGAPGAPGLQ

GMPGERGAAGLPGPKGERGDAGPKGADGAPGKDGVRGLAGPI
192 amino acids in length; comprising 4 ERGD
motifs;
```

From SEQ ID NO: 6, the sequence of ERGD-enriched monomer (SEQ ID NO: 2) has been derived.

```
Amino acid sequence of ERGD-enriched monomer
(SEQ ID NO: 2):
GAPGLQGAPGLQGMPGERGAAGLPGPKGERGDAGPKGADGAPGAPGLQGM

PGERGAAGLPGPKGERGDAGPKGADGAPGKDGVRGLAGPIGPPGERGAAG

LPGPKGERGDAGPKGADGAPGKDGVRGLAGPIGPPGPAGAPGAPGLQGMP

GERGAAGLPGPKGERGDAGPKGADGAPGKDGVRGLAGPP
189 amino acids in length; comprising 4 ERGD
motifs
```

Via standard subcloning methods multimers comprising the ERGD-enriched monomer have been prepared.

For example a multimer of this monomer comprising 3 repeats, i.e. ERGD-enriched trimer (SEQ ID NO: 3), preceded by GAP and extended with a glycine (G), was made. The sequence of the ERGD-enriched trimer comprising gelatine thus prepared is:

```
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)₃G
571 amino acids in length; comprising 12 ERGD
motifs
```

Also a multimer of this monomer comprising 5 repeats, i.e. ERGD-enriched pentamer (SEQ ID NO: 4), preceded by GAP and extended with a glycine (G), was made. The sequence of the ERGD-enriched pentamer comprising gelatine thus prepared is:

```
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)₅G
949 amino acids in length; comprising 20 ERGD
motifs
```

Example 2

Preparation of Microcarriers Beads

Polystyrene beads with an average diameter of 100 micrometers are used. The heterobifunctional cross-linking agent, BBA-EAC-NOS, is used to covalently immobilise gelatin onto polystyrene beads. The BBA-EAC-NOS is added to the polystyrene beads and allowed to adsorb. Next, gelatin is added and is allowed to react with the NOS synthetic polymer to produce covalent coupling to the spacer. Then the beads are photoactivated (at 320 nm) to covalently immobilise the spacer (and covalently coupled gelatin) to the polystyrene beads. Finally, loosely adherent gelatine is removed by overnight washing with the mild detergent Tween 20 in phosphate buffered saline (pH 7.2).

Cell Types and Culture Conditions

Green monkey kidney (Vero) cells, Chinese hamster ovary (CHO) cells, normal rat kidney fibroblast (NRK-49F) cells, and Madin Darby canine kidney (MDCK) cells were purchased from ATCC. All four cell types were passaged and maintained in 75 cm² flasks at 37 DEG C. in a 5% $CO_2$ environment. Vero and NRK-49F cells were cultured in Dulbecco's Modified Eagles's Medium (DMEM), CHO cells were cultured in Ham's F-12 Nutrient Mixture, and MDCK cells were cultured in Minimum Essential Medium (MEM) with Earle's salts.

With the Vero and CHO cells, the medium was supplemented with 10% fetal bovine serum (FBS), 2 mM L-glutamine, 20 mM HEPES buffer, 1 mM sodium pyruvate, 100 ug/ml streptomycin, and 100 units/ml penicillin (final pH 7.1). With the NRK-49F cells, the DMEM was supplemented with 5% FBS, 2 mM L-glutamine, 1 mM sodium pyruvate, non-essential amino acids (0.1 mM each), 100 μg/ml streptomycin, 100 units/ml penicillin, and 0.25 μg/ml of amphotericin B (final pH 7.1). With the MDCK cells, the MEM was supplemented with 10% FBS, 2 mM L-glutamine, non-essential amino acids (0.1 mM each), and 100 μg/ml streptomycin, 100 units/rill penicillin, and 0.25 μg/ml of amphotericin B (final pH 7.1).

In order to standardise the physiology of cells prior to each experiment, cells were passed into 150 cm² flasks 2 to 3 days prior to inoculation of microcarrier beads. Cells were trypsinised (0.05%, trypsin, 0.53 mM EDTA in PBS) for removal from the flasks. For the microcarrier experiments, the cells were centrifuged to remove the trypsin medium and resuspended to about 1.times.10⁶ cells/ml in culture medium. The viable cell concentration was deter mined by Trypan dye exclusion (0.4% Trypan blue in 0.9% saline).

Cell Culture and Assays in Spinner Flasks

For the cell attachment assay, 20 mg/ml of coated polystyrene beads were used and the cell concentration was 1.5.times.10⁵ cells/ml for each cell type.

Microcarriers were cultured with 100 ml cultures being maintained in 250 ml spinner vessels and stirred with suspended magnetic impellers (50 rpm).

The kinetics of cell attachment were assayed as a decrease in supernatant cell concentration. For sample removal the agitation was stopped briefly (about 30 seconds) at which time the microcarriers settled and a supernatant sample was removed for cell quantitation as described below.

For the cell counts, the cells were stained by mixing with an equal volume of crystal violet (0.1% w/w) in 0.1 M citric acid, and then counted with a hemocytometer. Cell depletion from the medium was used as an indicator of cells attached to beads.

To verify that cells removed from the medium were indeed attached to microcarriers (and not lysed), cells attached to microcarriers were quantitated at the end of each cell attachment assay. One ml aliquots of well-agitated carrier medium were removed, the microcarriers were allowed to settle, and the settled microcarriers were resuspended in crystal violet/citric acid as described above. After incubating 1 hour at 37 DEG C., the suspension was sheared by sucking into and out of a Pasteur pipette to release nuclei, which were quantitated with a haemocytometer.

ERGD containing gelatin (SEQ ID NO: 6) was used as a microcarrier coating according to the foregoing procedure and compared with a reference gelatin with sequence identifier number 2 having four RGD sequences as disclosed in US 2006/0241032. SEQ ID NO: 2 gave improved results in terms of numbers of cell depletion from the starting culture medium and also in terms of cell attachment to microcarriers. This improvement may be due to improved stability of the SEQ ID NO: 6 gelatine compared to the sequence with identifier number 2 as disclosed in US 2006/0241032.

Also gelatins comprising SEQ ID NO: 3 and SEQ ID NO: 4 are used as a microcarrier coating according to the foregoing procedure and compared with a trimer, a tetramer and a pentamer of XRGD-comprising gelatin with sequence identifier number 2 as disclosed in US 2006/0241032. Probably due to their improved stability, gelatins comprising SEQ ID NO: 3 and SEQ ID NO: 4 show improved cell attachment to microcarriers compared to the multimeric gelatins based on the sequence with identifier number 2 as disclosed in US 2006/0241032. Also particle size measurements of gelatins comprising SEQ ID NO: 3 and SEQ ID NO: 4 coated microcarriers after keeping the coated microcarriers for 24 hours and immediately after the cell attachment assay show a more homogeneous distribution of particle sizes compared to the multimeric gelatins based on the sequence with identifier number 2 as disclosed in US 2006/0241032.

Example 3

The following polypeptide was expressed in *Pichia pastoris*, using expression vectors and methods as described in the manual that comes with the Easy select *Pichia* expression kit version H (Invitrogen Corp.).

SEQ ID NO 5:
GAPGLQGMPGERGAAGLPGPKGDRGDAGPKGADGSPGKDGVRGLAGPIGP

PGAPGAPGSQGAPGLQGMPGERGAAGLPGPKGDRGDAGPKGADGSPGAPG

LQGMPGERGAAGLPGPKGDRGDAGPKGADGSPGKDGVRGLAGPIGPPLER

GAAGLPGPKGDRGDAGPKGADGSPGKDGVRGLAGPIGPPGPAGAPGAPGL

QGMPGERGAAGLPGPKGDRGDAGPKGADGSPGKDGVRGLAGPP

Polypeptides and polypeptide fragments secreted into the culture supernatant of recombinant *Pichia pastoris* were analyzed with LC-MS. In addition to the expected product, several smaller fragments were observed, as shown in the table below:

| Fragment | Size (Da) |
| --- | --- |
| 1 | 11170 |
| 2 | 12121 |
| 3 | 14466 |
| 4 | 17456 |
| 5 | 19291 |
| 6 | 19528 |
| 7 | 19742 |

The culture supernatant thus contained a large number of fragments of the recombinant polypeptide which were smaller than the full size polypeptide. These fragments were attributed to cleavage between D and R in the D/RGD various motifs.

To test this hypothesis an improved version of the polypeptide was made which did not contain DRGD motifs, but ERGD instead, referred to herein as SEQ ID NO: 6:

GAPGAPGLQGAPGLQGMPGERGAAGLPGPKGERGDAGPKGADSAPGAPGL

QGMPGERGAAGLPGPKGERGDAGPKGADGAPGKDGVRGLAGPIGPPGERG

AAGLPGPKGERGDAGPKGADGAPGKDGVRGLAGPIGPPGPAGAPGAPGLQ

GMPGERGAAGLPGPKGERGDAGPKGADGAPGKDGVRGLAGPI

Thus, SEQ ID NO: 6 does not contain DRGD motifs, but contains ERGD motifs instead.

The polypeptide was produced in recombinant *Pichia pastoris* using the same method as above and the culture supernatant was analysed.

No fragments were found that would expected to result from cleavage between E and R in E/RGD. Therefore, XRGD-enriched proteins with ERGD motifs instead of DRGD motifs are more stable.

The invention claimed is:

1. A recombinant gelatin polypeptide comprising an amino acid sequence with at least 90% sequence identity to SEQ ID NO:2.

2. A recombinant gelatin polypeptide according to claim 1, wherein the polypeptide comprises an amino acid sequence with at least 95% sequence identity to SEQ ID NO:2.

3. A recombinant gelatin polypeptide according to claim 1, wherein the polypeptide comprises the amino acid sequence of SEQ ID NO:2.

4. A controlled release composition comprising a recombinant gelatin according to claim 1.

5. A polymeric recombinant gelatin comprising or consisting of at least two repeats of the recombinant gelatin polypeptide according to claim 1.

6. The polymeric recombinant gelatin according to claim 5, wherein said repeats are identical in amino acid sequence.

7. The polymeric recombinant gelatin according to claim 1, wherein the repeats do not contain any intervening amino acids between the monomeric repeat units.

8. A cell support comprising a recombinant gelatin according to claim 1.

9. A method for producing a recombinant gelatin according to claim 1, said method comprising:
   a) preparing an expression vector comprising a nucleic acid sequence encoding a polypeptide according to claim 1 operably linked to a suitable promoter;
   b) expressing said nucleic acid sequence in a methylotrophic yeast;
   c) culturing said yeast under suitable fermentation conditions to allow expression of said nucleic acid sequence; and
   d) optionally purifying said polypeptide from the culture.

10. A method for inhibition of cancer metastasis, for prevention of platelet aggregation or to prevent tissue adhesion after surgery, comprising contacting a surgical site with a recombinant gelatin according to claim 1.

* * * * *

SEQUENCE LISTING

```
<160> NUMBER OF SEQ ID NOS: 6

<210> SEQ ID NO 1
<211> LENGTH: 1464
<212> TYPE: PRT
<213> ORGANISM: Homo sapiens P02452
<220> FEATURE:
<221> NAME/KEY: alpha1(I)chain
<222> LOCATION: (162)..(1218)
<220> FEATURE:
<221> NAME/KEY: triplehelical
<222> LOCATION: (179)..(1192)
<220> FEATURE:
<221> NAME/KEY: DRGD
<222> LOCATION: (744)..(777)
<220> FEATURE:
<221> NAME/KEY: PRGD
<222> LOCATION: (1092)..(1095)

<400> SEQUENCE: 1

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95
```

-continued

```
Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525
```

```
Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Gly Pro Ala Gly
545                 550                 555                 560

Gln Asp Gly Arg Pro Gly Pro Gly Pro Gly Ala Arg Gly Gln
                565                 570                 575

Ala Gly Val Met Gly Phe Pro Gly Pro Lys Gly Ala Gly Glu Pro
                580                 585                 590

Gly Lys Ala Gly Glu Arg Gly Val Pro Gly Pro Gly Ala Val Gly
            595                 600                 605

Pro Ala Gly Lys Asp Gly Glu Ala Gly Ala Gln Gly Pro Pro Gly Pro
        610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
                660                 665                 670

Ser Gly Ala Arg Gly Glu Arg Gly Phe Pro Gly Glu Arg Gly Val Gln
            675                 680                 685

Gly Pro Pro Gly Pro Ala Gly Pro Arg Gly Ala Asn Gly Ala Pro Gly
690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
                740                 745                 750

Ala Asp Gly Ser Pro Gly Lys Asp Gly Val Arg Gly Leu Thr Gly Pro
            755                 760                 765

Ile Gly Pro Pro Gly Pro Ala Gly Ala Pro Gly Asp Lys Gly Glu Ser
    770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
                820                 825                 830

Gly Ala Lys Gly Asp Ala Gly Pro Pro Gly Pro Ala Gly Pro Ala Gly
            835                 840                 845

Pro Pro Gly Pro Ile Gly Asn Val Gly Ala Pro Gly Ala Lys Gly Ala
        850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
                900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
        930                 935                 940

Ala Pro Gly Thr Pro Gly Pro Gln Gly Ile Ala Gly Gln Arg Gly Val
```

-continued

```
        945             950             955             960
Val Gly Leu Pro Gly Gln Arg Gly Glu Arg Gly Phe Pro Gly Leu Pro
                965             970             975
Gly Pro Ser Gly Glu Pro Gly Lys Gln Gly Pro Ser Gly Ala Ser Gly
                980             985             990
Glu Arg Gly Pro Pro Gly Pro Met Gly Pro Pro Gly Leu Ala Gly Pro
                995             1000            1005
Pro Gly Glu Ser Gly Arg Gly Ala Pro Gly Ala Glu Gly Ser
        1010            1015            1020
Pro Gly Arg Asp Gly Ser Pro Gly Ala Lys Gly Asp Arg Gly Glu
        1025            1030            1035
Thr Gly Pro Ala Gly Pro Gly Ala Pro Gly Ala Pro Gly Ala
        1040            1045            1050
Pro Gly Pro Val Gly Pro Ala Gly Lys Ser Gly Asp Arg Gly Glu
        1055            1060            1065
Thr Gly Pro Ala Gly Pro Ala Gly Pro Val Gly Pro Val Gly Ala
        1070            1075            1080
Arg Gly Pro Ala Gly Pro Gln Gly Pro Arg Gly Asp Lys Gly Glu
        1085            1090            1095
Thr Gly Glu Gln Gly Asp Arg Gly Ile Lys Gly His Arg Gly Phe
        1100            1105            1110
Ser Gly Leu Gln Gly Pro Pro Gly Pro Pro Gly Ser Pro Gly Glu
        1115            1120            1125
Gln Gly Pro Ser Gly Ala Ser Gly Pro Ala Gly Pro Arg Gly Pro
        1130            1135            1140
Pro Gly Ser Ala Gly Ala Pro Gly Lys Asp Gly Leu Asn Gly Leu
        1145            1150            1155
Pro Gly Pro Ile Gly Pro Pro Gly Pro Arg Gly Arg Thr Gly Asp
        1160            1165            1170
Ala Gly Pro Val Gly Pro Pro Gly Pro Pro Gly Pro Pro Gly Pro
        1175            1180            1185
Pro Gly Pro Pro Ser Ala Gly Phe Asp Phe Ser Phe Leu Pro Gln
        1190            1195            1200
Pro Pro Gln Glu Lys Ala His Asp Gly Gly Arg Tyr Tyr Arg Ala
        1205            1210            1215
Asp Asp Ala Asn Val Val Arg Asp Arg Asp Leu Glu Val Asp Thr
        1220            1225            1230
Thr Leu Lys Ser Leu Ser Gln Ile Glu Asn Ile Arg Ser Pro
        1235            1240            1245
Glu Gly Ser Arg Lys Asn Pro Ala Arg Thr Cys Arg Asp Leu Lys
        1250            1255            1260
Met Cys His Ser Asp Trp Lys Ser Gly Glu Tyr Trp Ile Asp Pro
        1265            1270            1275
Asn Gln Gly Cys Asn Leu Asp Ala Ile Lys Val Phe Cys Asn Met
        1280            1285            1290
Glu Thr Gly Glu Thr Cys Val Tyr Pro Thr Gln Pro Ser Val Ala
        1295            1300            1305
Gln Lys Asn Trp Tyr Ile Ser Lys Asn Pro Lys Asp Lys Arg His
        1310            1315            1320
Val Trp Phe Gly Glu Ser Met Thr Asp Gly Phe Gln Phe Glu Tyr
        1325            1330            1335
Gly Gly Gln Gly Ser Asp Pro Ala Asp Val Ala Ile Gln Leu Thr
        1340            1345            1350
```

-continued

```
Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 2
<211> LENGTH: 189
<212> TYPE: PRT
<213> ORGANISM: Artificial
<220> FEATURE:
<223> OTHER INFORMATION: XRGD enriched monomer

<400> SEQUENCE: 2

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Ala Gly Pro Lys Gly Ala Asp Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro
            180                 185

<210> SEQ ID NO 3
<211> LENGTH: 567
<212> TYPE: PRT
<213> ORGANISM: Artificial
<220> FEATURE:
<223> OTHER INFORMATION: XRGD enriched multimer (trimer)

<400> SEQUENCE: 3
```

-continued

```
Gly Ala Pro Gly Leu Gln Gly Ala Pro Gly Leu Gln Gly Met Pro Gly
1               5                   10                  15
Glu Arg Gly Ala Ala Gly Leu Pro Gly Pro Lys Gly Glu Arg Gly Asp
            20                  25                  30
Ala Gly Pro Lys Gly Ala Asp Gly Ala Pro Gly Ala Pro Gly Leu Gln
            35                  40                  45
Gly Met Pro Gly Glu Arg Gly Ala Ala Gly Leu Pro Gly Pro Lys Gly
        50                  55                  60
Glu Arg Gly Asp Ala Gly Pro Lys Gly Ala Asp Gly Ala Pro Gly Lys
65                  70                  75                  80
Asp Gly Val Arg Gly Leu Ala Gly Pro Ile Gly Pro Pro Gly Glu Arg
                85                  90                  95
Gly Ala Ala Gly Leu Pro Gly Pro Lys Gly Glu Arg Gly Asp Ala Gly
                100                 105                 110
Pro Lys Gly Ala Asp Gly Ala Pro Gly Lys Asp Gly Val Arg Gly Leu
        115                 120                 125
Ala Gly Pro Ile Gly Pro Pro Gly Pro Ala Gly Ala Pro Gly Ala Pro
        130                 135                 140
Gly Leu Gln Gly Met Pro Gly Glu Arg Gly Ala Ala Gly Leu Pro Gly
145                 150                 155                 160
Pro Lys Gly Glu Arg Gly Asp Ala Gly Pro Lys Gly Ala Asp Gly Ala
                165                 170                 175
Pro Gly Lys Asp Gly Val Arg Gly Leu Ala Gly Pro Pro Gly Ala Pro
                180                 185                 190
Gly Leu Gln Gly Ala Pro Gly Leu Gln Gly Met Pro Gly Glu Arg Gly
        195                 200                 205
Ala Ala Gly Leu Pro Gly Pro Lys Gly Glu Arg Gly Asp Ala Gly Pro
        210                 215                 220
Lys Gly Ala Asp Gly Ala Pro Gly Ala Pro Gly Leu Gln Gly Met Pro
225                 230                 235                 240
Gly Glu Arg Gly Ala Ala Gly Leu Pro Gly Pro Lys Gly Glu Arg Gly
                245                 250                 255
Asp Ala Gly Pro Lys Gly Ala Asp Gly Ala Pro Gly Lys Asp Gly Val
                260                 265                 270
Arg Gly Leu Ala Gly Pro Ile Gly Pro Pro Gly Glu Arg Gly Ala Ala
        275                 280                 285
Gly Leu Pro Gly Pro Lys Gly Glu Arg Gly Asp Ala Gly Pro Lys Gly
        290                 295                 300
Ala Asp Gly Ala Pro Gly Lys Asp Gly Val Arg Gly Leu Ala Gly Pro
305                 310                 315                 320
Ile Gly Pro Pro Gly Pro Ala Gly Ala Pro Gly Ala Pro Gly Leu Gln
                325                 330                 335
Gly Met Pro Gly Glu Arg Gly Ala Ala Gly Leu Pro Gly Pro Lys Gly
        340                 345                 350
Glu Arg Gly Asp Ala Gly Pro Lys Gly Ala Asp Gly Ala Pro Gly Lys
        355                 360                 365
Asp Gly Val Arg Gly Leu Ala Gly Pro Pro Gly Ala Pro Gly Leu Gln
        370                 375                 380
Gly Ala Pro Gly Leu Gln Gly Met Pro Gly Glu Arg Gly Ala Ala Gly
385                 390                 395                 400
Leu Pro Gly Pro Lys Gly Glu Arg Gly Asp Ala Gly Pro Lys Gly Ala
                405                 410                 415
Asp Gly Ala Pro Gly Ala Pro Gly Leu Gln Gly Met Pro Gly Glu Arg
                420                 425                 430
```

```
Gly Ala Ala Gly Leu Pro Gly Pro Lys Gly Glu Arg Gly Asp Ala Gly
            435                 440                 445

Pro Lys Gly Ala Asp Gly Ala Pro Gly Lys Asp Gly Val Arg Gly Leu
    450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
                485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
            515                 520                 525

Gly Glu Arg Gly Ala Ala Gly Leu Pro Gly Pro Lys Gly Glu Arg Gly
        530                 535                 540

Asp Ala Gly Pro Lys Gly Ala Asp Gly Ala Pro Gly Lys Asp Gly Val
545                 550                 555                 560

Arg Gly Leu Ala Gly Pro Pro
                565

<210> SEQ ID NO 4
<211> LENGTH: 945
<212> TYPE: PRT
<213> ORGANISM: Artificial
<220> FEATURE:
<223> OTHER INFORMATION: XRGD enriched multimer (pentamer)

<400> SEQUENCE: 4

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
            20                  25                  30

Ala Gly Pro Lys Gly Ala Asp Gly Ala Pro Gly Ala Pro Gly Leu Gln
        35                  40                  45

Gly Met Pro Gly Glu Arg Gly Ala Ala Gly Leu Pro Gly Pro Lys Gly
    50                  55                  60

Glu Arg Gly Asp Ala Gly Pro Lys Gly Ala Asp Gly Ala Pro Gly Lys
65                  70                  75                  80

Asp Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Ala Gly
            100                 105                 110

Pro Lys Gly Ala Asp Gly Ala Pro Gly Lys Asp Gly Val Arg Gly Leu
        115                 120                 125

Ala Gly Pro Ile Gly Pro Pro Gly Pro Ala Gly Ala Pro Gly Ala Pro
    130                 135                 140

Gly Leu Gln Gly Met Pro Gly Glu Arg Gly Ala Ala Gly Leu Pro Gly
145                 150                 155                 160

Pro Lys Gly Glu Arg Gly Asp Ala Gly Pro Lys Gly Ala Asp Gly Ala
                165                 170                 175

Pro Gly Lys Asp Gly Val Arg Gly Leu Ala Gly Pro Pro Gly Ala Pro
            180                 185                 190

Gly Leu Gln Gly Ala Pro Gly Leu Gln Gly Met Pro Gly Glu Arg Gly
        195                 200                 205

Ala Ala Gly Leu Pro Gly Pro Lys Gly Glu Arg Gly Asp Ala Gly Pro
    210                 215                 220
```

-continued

```
Lys Gly Ala Asp Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
            245                 250                 255

Asp Ala Gly Pro Lys Gly Ala Asp Gly Ala Pro Gly Lys Asp Gly Val
        260                 265                 270

Arg Gly Leu Ala Gly Pro Ile Gly Pro Pro Gly Glu Arg Gly Ala Ala
    275                 280                 285

Gly Leu Pro Gly Pro Lys Gly Glu Arg Gly Asp Ala Gly Pro Lys Gly
290                 295                 300

Ala Asp Gly Ala Pro Gly Lys Asp Gly Val Arg Gly Leu Ala Gly Pro
305                 310                 315                 320

Ile Gly Pro Pro Gly Pro Ala Gly Ala Pro Gly Ala Pro Gly Leu Gln
                325                 330                 335

Gly Met Pro Gly Glu Arg Gly Ala Ala Gly Leu Pro Gly Pro Lys Gly
            340                 345                 350

Glu Arg Gly Asp Ala Gly Pro Lys Gly Ala Asp Gly Ala Pro Gly Lys
        355                 360                 365

Asp Gly Val Arg Gly Leu Ala Gly Pro Gly Ala Pro Gly Leu Gln
    370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Ala Gly Pro Lys Gly Ala
                405                 410                 415

Asp Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Ala Gly
        435                 440                 445

Pro Lys Gly Ala Asp Gly Ala Pro Gly Lys Asp Gly Val Arg Gly Leu
    450                 455                 460

Ala Gly Pro Ile Gly Pro Pro Gly Glu Arg Gly Ala Ala Gly Leu Pro
465                 470                 475                 480

Gly Pro Lys Gly Glu Arg Gly Asp Ala Gly Pro Lys Gly Ala Asp Gly
                485                 490                 495

Ala Pro Gly Lys Asp Gly Val Arg Gly Leu Ala Gly Pro Ile Gly Pro
            500                 505                 510

Pro Gly Pro Ala Gly Ala Pro Gly Ala Pro Gly Leu Gln Gly Met Pro
        515                 520                 525

Gly Glu Arg Gly Ala Ala Gly Leu Pro Gly Pro Lys Gly Glu Arg Gly
    530                 535                 540

Asp Ala Gly Pro Lys Gly Ala Asp Gly Ala Pro Gly Lys Asp Gly Val
545                 550                 555                 560

Arg Gly Leu Ala Gly Pro Pro Gly Ala Pro Gly Leu Gln Gly Ala Pro
                565                 570                 575

Gly Leu Gln Gly Met Pro Gly Glu Arg Gly Ala Ala Gly Leu Pro Gly
            580                 585                 590

Pro Lys Gly Glu Arg Gly Asp Ala Gly Pro Lys Gly Ala Asp Gly Ala
        595                 600                 605

Pro Gly Ala Pro Gly Leu Gln Gly Met Pro Gly Glu Arg Gly Ala Ala
    610                 615                 620

Gly Leu Pro Gly Pro Lys Gly Glu Arg Gly Asp Ala Gly Pro Lys Gly
625                 630                 635                 640

Ala Asp Gly Ala Pro Gly Lys Asp Gly Val Arg Gly Leu Ala Gly Pro
                645                 650                 655
```

Ile Gly Pro Pro Gly Glu Arg Gly Ala Ala Gly Leu Pro Gly Pro Lys
             660                 665                 670

Gly Glu Arg Gly Asp Ala Gly Pro Lys Gly Ala Asp Gly Ala Pro Gly
             675                 680                 685

Lys Asp Gly Val Arg Gly Leu Ala Gly Pro Ile Gly Pro Pro Gly Pro
    690                 695                 700

Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Ala Gly
                725                 730                 735

Pro Lys Gly Ala Asp Gly Ala Pro Gly Lys Asp Gly Val Arg Gly Leu
             740                 745                 750

Ala Gly Pro Pro Gly Ala Pro Gly Leu Gln Gly Ala Pro Gly Leu Gln
             755                 760                 765

Gly Met Pro Gly Glu Arg Gly Ala Ala Gly Leu Pro Gly Pro Lys Gly
    770                 775                 780

Glu Arg Gly Asp Ala Gly Pro Lys Gly Ala Asp Gly Ala Pro Gly Ala
785                 790                 795                 800

Pro Gly Leu Gln Gly Met Pro Gly Glu Arg Gly Ala Ala Gly Leu Pro
                805                 810                 815

Gly Pro Lys Gly Glu Arg Gly Asp Ala Gly Pro Lys Gly Ala Asp Gly
             820                 825                 830

Ala Pro Gly Lys Asp Gly Val Arg Gly Leu Ala Gly Pro Ile Gly Pro
             835                 840                 845

Pro Gly Glu Arg Gly Ala Ala Gly Leu Pro Gly Pro Lys Gly Glu Arg
    850                 855                 860

Gly Asp Ala Gly Pro Lys Gly Ala Asp Gly Ala Pro Gly Lys Asp Gly
865                 870                 875                 880

Val Arg Gly Leu Ala Gly Pro Ile Gly Pro Pro Gly Pro Ala Gly Ala
                885                 890                 895

Pro Gly Ala Pro Gly Leu Gln Gly Met Pro Gly Glu Arg Gly Ala Ala
             900                 905                 910

Gly Leu Pro Gly Pro Lys Gly Glu Arg Gly Asp Ala Gly Pro Lys Gly
             915                 920                 925

Ala Asp Gly Ala Pro Gly Lys Asp Gly Val Arg Gly Leu Ala Gly Pro
    930                 935                 940

Pro
945

<210> SEQ ID NO 5
<211> LENGTH: 243
<212> TYPE: PRT
<213> ORGANISM: unknown
<220> FEATURE:
<223> OTHER INFORMATION: DRGD comprising monomer

<400> SEQUENCE: 5

Gly Ala Pro Gly Leu Gln Gly Met Pro Gly Glu Arg Gly Ala Ala Gly
1               5                   10                  15

Leu Pro Gly Pro Lys Gly Asp Arg Gly Asp Ala Gly Pro Lys Gly Ala
                20                  25                  30

Asp Gly Ser Pro Gly Lys Asp Gly Val Arg Gly Leu Ala Gly Pro Ile
            35                  40                  45

Gly Pro Pro Gly Ala Pro Gly Ala Pro Gly Ser Gln Gly Ala Pro Gly
        50                  55                  60

```
Leu Gln Gly Met Pro Gly Glu Arg Gly Ala Ala Gly Leu Pro Gly Pro
 65                  70                  75                  80

Lys Gly Asp Arg Gly Asp Ala Gly Pro Lys Gly Ala Asp Gly Ser Pro
                 85                  90                  95

Gly Ala Pro Gly Leu Gln Gly Met Pro Gly Glu Arg Gly Ala Ala Gly
            100                 105                 110

Leu Pro Gly Pro Lys Gly Asp Arg Gly Asp Ala Gly Pro Lys Gly Ala
        115                 120                 125

Asp Gly Ser Pro Gly Lys Asp Gly Val Arg Gly Leu Ala Gly Pro Ile
130                 135                 140

Gly Pro Pro Gly Glu Arg Gly Ala Ala Gly Leu Pro Gly Pro Lys Gly
145                 150                 155                 160

Asp Arg Gly Asp Ala Gly Pro Lys Gly Ala Asp Gly Ser Pro Gly Lys
                165                 170                 175

Asp Gly Val Arg Gly Leu Ala Gly Pro Ile Gly Pro Pro Gly Pro Ala
            180                 185                 190

Gly Ala Pro Gly Ala Pro Gly Leu Gln Gly Met Pro Gly Glu Arg Gly
            195                 200                 205

Ala Ala Gly Leu Pro Gly Pro Lys Gly Asp Arg Gly Asp Ala Gly Pro
        210                 215                 220

Lys Gly Ala Asp Gly Ser Pro Gly Lys Asp Gly Val Arg Gly Leu Ala
225                 230                 235                 240

Gly Pro Pro

<210> SEQ ID NO 6
<211> LENGTH: 192
<212> TYPE: PRT
<213> ORGANISM: Artificial
<220> FEATURE:
<223> OTHER INFORMATION: ERGD comprising sequence

<400> SEQUENCE: 6

Gly Ala Pro Gly Ala Pro Gly Leu Gln Gly Ala Pro Gly Leu Gln Gly
 1               5                  10                  15

Met Pro Gly Glu Arg Gly Ala Ala Gly Leu Pro Gly Pro Lys Gly Glu
                 20                  25                  30

Arg Gly Asp Ala Gly Pro Lys Gly Ala Asp Gly Ala Pro Gly Ala Pro
             35                  40                  45

Gly Leu Gln Gly Met Pro Gly Glu Arg Gly Ala Ala Gly Leu Pro Gly
         50                  55                  60

Pro Lys Gly Glu Arg Gly Asp Ala Gly Pro Lys Gly Ala Asp Gly Ala
 65                  70                  75                  80

Pro Gly Lys Asp Gly Val Arg Gly Leu Ala Gly Pro Ile Gly Pro Pro
                 85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175
```

```
Asp Gly Ala Pro Gly Lys Asp Gly Val Arg Gly Leu Ala Gly Pro Ile
            180                 185                 190
```